Figure 1:
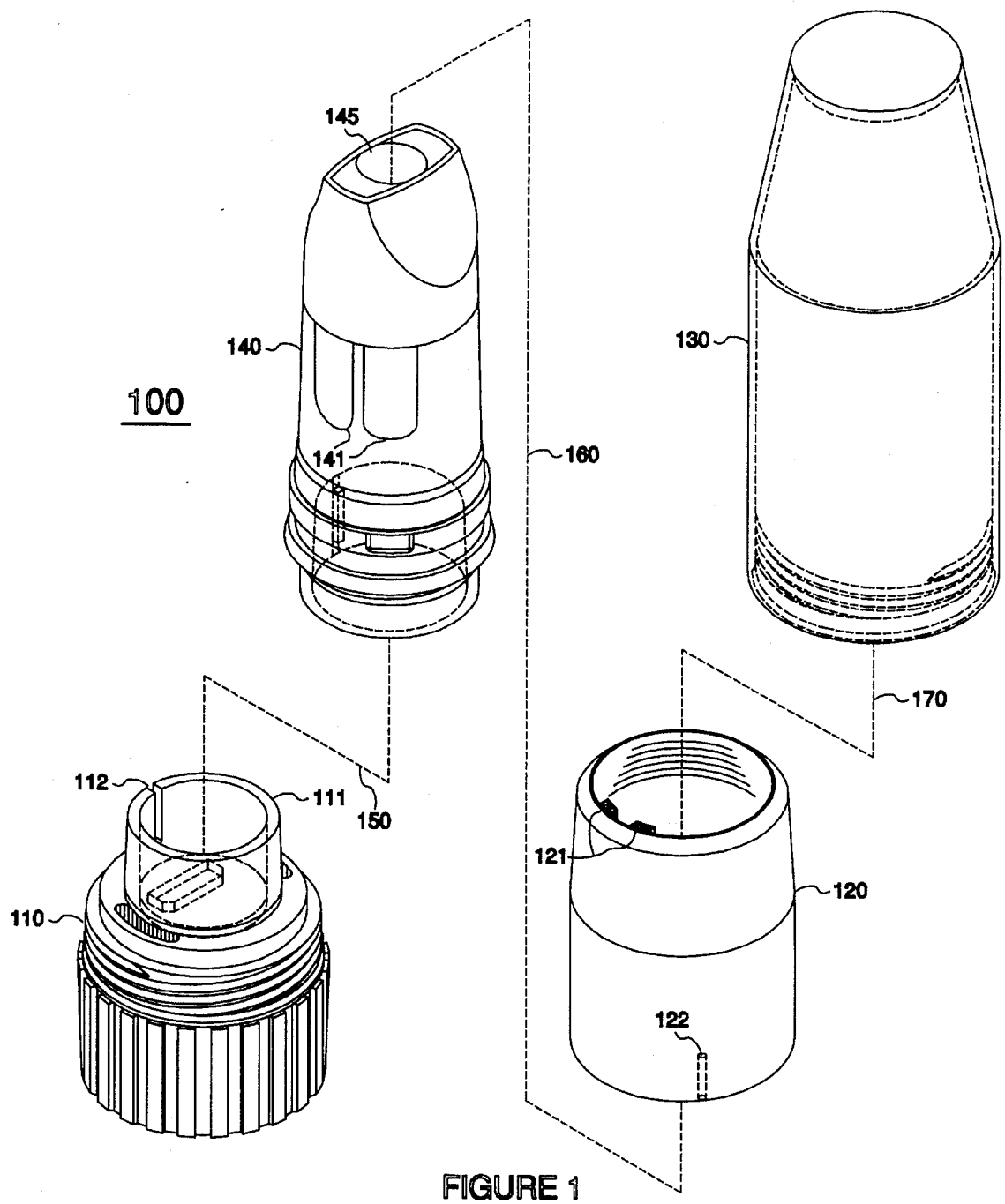

United States Patent [19]
Wolf et al.

[11] Patent Number: 5,505,195
[45] Date of Patent: Apr. 9, 1996

[54] DRY POWDER INHALANT DEVICE WITH DOSAGE AND AIR FLOW MONITOR

[75] Inventors: James L. Wolf; Daniel V. Sallis, both of Littleton, Colo.

[73] Assignee: Medtrac Technologies Inc., Lakewood, Colo.

[21] Appl. No.: 122,126

[22] Filed: Sep. 16, 1993

[51] Int. Cl.⁶ .................. A61M 15/00; A61M 16/10; B05D 7/14; B65D 83/06
[52] U.S. Cl. .................. 128/203.15; 128/203.14; 128/200.23
[58] Field of Search .................. 128/200.23, 203.15, 128/203.19, 203.21, 203.24, 203.14, 203.12

[56] References Cited

U.S. PATENT DOCUMENTS

| | | | |
|---|---|---|---|
| 4,604,847 | 8/1986 | Moulding, Jr. et al. | 128/203.15 |
| 4,984,158 | 4/1991 | Hillsman | 128/200.23 |
| 5,020,527 | 6/1991 | Dessertine | 128/200.23 |
| 5,167,506 | 12/1992 | Kilis et al. | 128/200.23 |
| 5,284,133 | 2/1994 | Burns et al. | 128/203.15 |
| 5,363,842 | 11/1994 | Mishelevich et al. | 128/205.23 |
| 5,392,768 | 2/1995 | Johansson et al. | 128/204.23 |
| 5,394,866 | 3/1995 | Ritson et al. | 128/200.14 |

FOREIGN PATENT DOCUMENTS

| | | | |
|---|---|---|---|
| 2262452 | 6/1993 | United Kingdom | 128/200.23 |
| 8602275 | 4/1986 | WIPO | 128/200.23 |
| 8704354 | 7/1987 | WIPO | 128/200.23 |
| 9010470 | 9/1990 | WIPO | 128/203.15 |
| 9106334 | 5/1991 | WIPO | 128/200.23 |
| 9207599 | 5/1992 | WIPO | 128/203.15 |
| 9217231 | 10/1992 | WIPO | 128/200.23 |

Primary Examiner—Kimberly L. Asher
Attorney, Agent, or Firm—Edwin H. Crabtree; Donald W. Margolis; Ramon L. Pizarro

[57] ABSTRACT

A dry powder inhalant device adapted for mounting on a conventional medication dry powder dispenser having a mouthpiece incorporated in one end of the dispenser. The device designed for monitoring prescribed dosages of dry powder medication received through the mouthpiece, the lips and into the mouth, throat, and respiratory system of a user of the device. The device includes an electronic housing mounted on the dispenser for computing and recording when a proper amount of dry powder is released inside the dispenser, when a proper amount of air flow is inhaled through the dispenser for mixing with the dry powder, and when each dispenser or dry powder container is removed and replaced on the electronic housing. The dispenser, in one embodiment, includes an activation sheath received around and secured to a portion of the dispenser. A lower end of the sheath abuts the electronic housing with the mouthpiece extending upwardly and through an upper end of the sheath. The electronic housing includes a first and second proximity reed switch for recording when a proper dosage of dry powder is released inside the dispenser by properly rotating the sheath and dispenser a fixed distance in one direction on the electronic housing and rotating the sheath and dispenser a fixed distance in an opposite direction. The electronic housing also includes a fast response thermistor for measuring when sufficient air flow is being drawn into the housing, into the dispenser and mixed with the dry powder and out the mouthpiece when using the device.

8 Claims, 8 Drawing Sheets

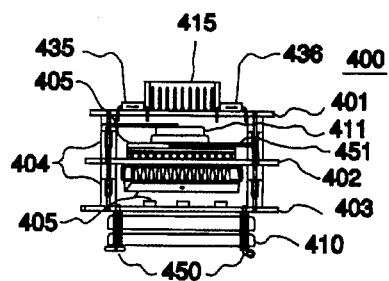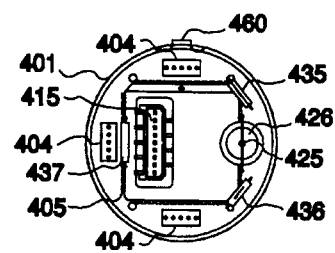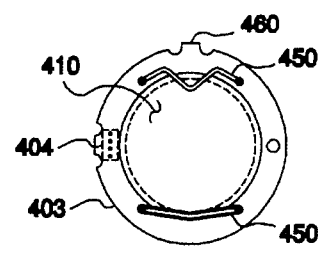
FIGURE 4a  FIGURE 4b  FIGURE 4c
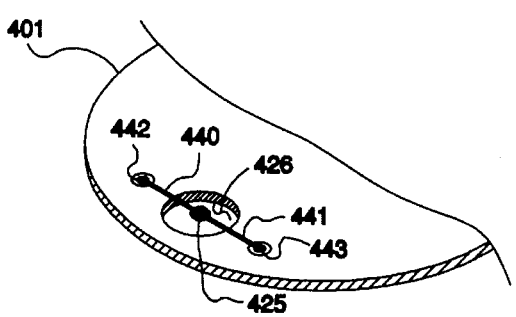
FIGURE 4d
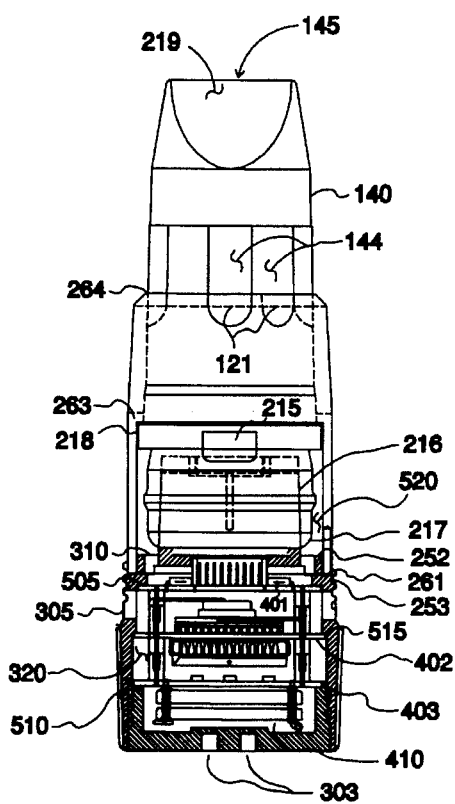
FIGURE 5

DRY POWDER INHALANT DEVICE WITH DOSAGE AND AIR FLOW MONITOR

BACKGROUND OF THE INVENTION

1. Related Inventions

The present invention is related to the following copending applications, Medication Inhalant Device having and Ser. No. 08/122,128 and filed on Sep. 16, 1993, and Peak Flow Chronolog Apparatus having Ser. No. 08/140,752 and filed on Oct. 22, 1993.

2. Field of the Invention

The present invention relates to the field of medication monitoring and, more particularly, to a device which attaches to conventional medication delivery systems, such as dry powder medication dispensing package, for positive recording of prescribed dosages and system to analyze chronologic report.

3. Discussion of Prior Art

In a prior issued patent entitled "Timed Pill Monitor and Dispenser", U.S. Pat. No. 4,662,537, issued on May 5, 1987 to the present inventor, a medication monitor was disclosed wherein pre-packaged medication "pills" were placed into compartmental chambers on a hand held device for later usage. Such a system is useful for recording the event of each time a chamber was accessed and a pill removed for prescribed medication.

The present invention provides a positive indication that dry power medication has been properly dispensed, inhaled and logged.

Prior to the filing of this application, the inventor conducted a patentability investigation for a system that monitors the administration of proscribed dry power drugs, and provide a chronological report for all activity therewith. The following patents in addition to the above stated patent were uncovered in the search:

| Inventor | Reg. No. | Date |
|---|---|---|
| Kehr et al. | 5,200,891 | Apr. 6, 1993 |
| Johnson, IV et al. | 5,133,343 | Jul. 28, 1992 |
| Wood et al. | 5,097,429 | Mar. 17, 1992 |
| Moulding | 5,042,685 | Aug. 27, 1991 |
| Foley | 5,042,467 | Aug. 27, 1991 |
| Moulding | 4,869,352 | Sep. 26, 1989 |
| Behl | 4,473,884 | Sep. 25, 1984 |
| Moulding | 4,460,106 | Jul. 17, 1984 |

Discussion of discovered prior art:

The patent issued to Kehr et al (U.S. Pat. No. 5,200,891) pertains to a device having a plurality of compartments, each of which store medication pills and an electrical signaling system to emit medication alert signals. The disclosed signals indicate that medication should be taken, from which compartment and the quantity. The device of Kehr has a high degree of inter-action between the user and its operation by selecting push-buttons and reading messages on the device display.

In the apparatus of Johnson, IV et al. (U.S. Pat. No. 5,133,343) has a user's mouthpiece housed therein and automatically actuated commercially available and replaceable inhalers for discharging a medicated vapor. The primary objective of the the Johnson, IV invention is to provide a device for actuating an inhaler in response to inhalation by a user.

The 1992 patent issued to Wood et al. (U.S. Pat. No. 5,097,429) pertains to a user programmable microprocessor based apparatus which acts as a reminder to a medication schedule of events. When the user programs parameters relating to intervals of medication, the device prompts the user by signaling an alarm.

The third patent of Moulding (U.S. Pat. No. 5,042,685, Aug. 27, 1991) manages the dispensing of pills. While the second patent of Moulding (U.S. Pat. No. 4,869,352, Sep. 26, 1989) pertains to conforming to the shape and size of a pill for dispensing, and Moulding's Jul. 17, 1984 patent (U.S. Pat. No. 4,460,106) concerns the counting of pills being dispensed.

The Foley patent (U.S. Pat. No. 5,042,467) teaches improved misting of inhaler medication which provides warning by means of sonic signalling if the user inhales too vigorously.

The 1984 patent issued to Behl (U.S. Pat. No. 4,473,884) sets forth an electronically controlled medication dispenser with a second pharmacy programmer used to program the dispenser. The dispenser includes a plurality of compartments for storage of tablets or pills. Each compartment has associated indicators which activate and are announced audibly, first softly, and then increasingly in magnitude to a programmed time schedule. The user would then open the indicated compartment and take the suggested dosage of medication. The pharmacy disktop sized programmer may program the electronic dispenser to optimize the medication schedule with the user's personal eating and sleeping habits information is programmed into a non-volatile memory within None of the above approaches disclosed an approach for chronologically recording the administration of dry powder medication as a matter of positive fact as to the dispensing and inhalation. And, preserving recorded data for later retrieval and analysis of a user's historical medication dispensing activity so doctors may better make prognosis based on drug proscribing.

SUMMARY OF THE INVENTION

An object of the present invention is to provide a portable, highly miniaturized device which when attached to a conventional medication dry powder dispenser will positively monitor the administration of the medication.

Another object of the invention is the device includes a sensor placed in an air flow path for measuring when sufficient air flow is being drawn into the dispenser, mixed with the dry powder and out a mouthpiece of the dispenser.

Still another object of the dry powder inhalant device is an electronic package in a housing of the invention makes a record of when a proper dosage of dry powder is released in the dispenser, when sufficient air flow is received in the dispenser when the dry powder is released and when the dispenser is removed and replaced on the electronic package.

Yet another object of the invention is the electronic package of the dry powder inhalant device can be periodically connected to a system in a Doctor's office, hospital, and like medical facilities to up-load stored information and analyze the chronologic report stored within. This may be accomplish directly or through a telephone and a modem.

The dry powder medication inhalant device is adapted for mounting on a conventional medication dry powder dispenser having a mouthpiece incorporated in one end of the dispenser. The device is designed for monitoring prescribed dosages of dry powder medication received through the mouthpiece, the lips and into the mouth, throat, and respiratory system of a user of the device. The invention includes an electronic housing mounted on the dispenser for computing and recording when a proper amount of dry powder is released inside the dispenser, when a proper amount of air flow is inhaled through the dispenser for mixing with the dry powder, and when each dispenser or dry powder container is removed and replaced on the electronic housing. The dispenser, in one embodiment, includes an activation sheath received around and secured to a portion of the dispenser. A lower end of the sheath abuts the electronic housing with the mouthpiece extending upwardly and through an upper end of the sheath. The electronic housing includes a first and second proximity reed switch for recording when a proper dosage of dry powder is released inside the dispenser by properly rotating the sheath and dispenser a fixed distance in one direction on the electronic housing and rotating the sheath and dispenser a fixed distance in an opposite direction. The electronic housing also includes a fast response thermistor for measuring when sufficient air flow is being drawn into the housing, into the dispenser and mixed with the dry powder and out the mouthpiece when using the device.

These and other objects of the present invention will become apparent to those skilled in the art from the following detailed description, showing the contemplated novel construction, combination, and elements as herein described, and more particularly defined by the appended claims, it being understood that changes in the precise embodiments to the herein disclosed invention are meant to be included as coming within the scope of the claims, except insofar as they may be precluded by the prior art.

BRIEF DESCRIPTION OF THE DRAWINGS

The accompanying drawings illustrate complete preferred embodiments of the present invention according to the best modes presently devised for the practical application of the principles thereof, and in which:

FIG. 1 sets forth a perspective view of present invention showing sanitation cover and activation sheath removed.

FIG. **2*a*** is a side planar view of a conventional medication dry powder inhalant package.

FIG. **2*b* is an end planar view of FIG. 2*a*.**

FIG. **2*c* is a side planar view of FIG. 2*a*** with cover and end cap removed showing main body of conventional dry powder medication inhalant package.

FIG. **2*d*** is a side planar view of the device of the present invention with sanitation cover and activation sheath detached from electronics housing end cap, and showing path where conventional dry powder medication inhalant package would be placed.

FIG. **2*e*** is a side planar view of the device of the present invention fully assembled with conventional dry powder medication inhalant package within.

FIG. **2*f* is an end planar view of FIG. 2*e*.**

FIGS. **3*a*–3*f*** are cross-sectional views showing the inner chambers and air passages of the present invention.

FIG. **4*a*** is a side planar view of the electronics assembly and sensing elements of the present invention.

FIG. **4*b*** is a top planar view of the electronics assembly and sensing elements of the present invention.

FIG. **4*c*** is a bottom planar view of the electronics assembly of the present invention.

FIG. **4*d* is a partial perspective view of FIG. 4*b*** showing detail of electronic main sensing element.

FIG. 5 is a side planar illustration showing the device of FIG. **2*e*** as it would be used by a patient and showing the interrelationships of air passage chambers.

FIG. 6 sets forth a perspective illustration of an alternate embodiment showing a different manufacturer of conventional dry powder medication inhalant package.

FIG. 7 is a schematic block diagram of the electronics of the present invention.

FIG. 8 sets forth a state table for the control circuit of FIG. 7.

FIG. 9 sets forth an illustration of the system of the present invention being connected to a data retrieval device.

FIG. 10 sets forth a bottom perspective illustration of a second embodiment showing an information display of the device of the present invention.

DESCRIPTION OF THE PREFERRED EMBODIMENT

In FIG. 1, the electronic medicated dry powder inhalant apparatus 100 of the present invention is shown with main components separated from electronics housing end cap 110. A conventionally available medicated dry powder metered dose inhalant dispenser 140 is fitted onto electronic housing 110 as dotted line 150 indicates, over tubular boss 111 with alignment key slot 112 properly positioned. Note that metered dose inhalant dispenser has an outlet 145 at its top. Activation sheath 120 fits over metered dose inhalant dispenser 140 snugly as dotted line 160 indicates and positions alignment keys 121 to properly mate with fluted surfaces 141 of dispenser package. With sheath 120 properly installed, magnet 122 (embedded in sheath wall) is aligned with electronics in the housing 110. Sanitation protective cover 130 fits over activation sheath 120 and metered dose inhalant dispenser 140 and attaches to electronics housing 110 to protect the apparatus while unit is not being used. A more detailed discussion of these components are revealed in FIG. **2*a*–2*f*.**

In FIG. **2*a*–2*f* shows detail on how a conventional medicated dry powder dispenser package is incorporated in the present invention. FIG. 2*a* shows the dispenser package 200 as it is available from the manufacture Astra Pharma Inc., known as Pulmicort Turbuhaler®. FIG. 2*b* is an end planar view of FIG. 2*a* showing the grooved hand grip 205 of end cap 210 for the easy holding of the dispensing package. FIG. 2*c* shows an exploded side planar view of the dispenser package 200 in its three main components; end cap 210, metered dose inhalant dispenser 140, and sanitary cover 220. Metered dose inhalant dispenser 140 has air inlet orifices 215 which shall be discussed later (a second orifice 215** is on other side of dispenser housing not shown).

FIG. **2*d* shows a side planar exploded view of the device of the present invention 100 comprising three main components; electronics housing end cap 110, activation sheath 120 and sanitation cover 130. In FIG. 2*e* is a side planar view of FIG. 2*d* fully assembled and incorporated within, the meter dose dispenser 140 of FIG. 2*c*. The FIG. 2*f* shows an end planar view of FIG. 2*e* showing a groved hand grip 290 in the electronic housing 110** for the easy holding and operating of the apparatus of the present invention.

Hence, under the teachings of the present invention, is shown in FIG. **2*a* through 2*f*** how a conventional dry powder dispensing package containing medicated metered dose inhaling powder can be incorporated into the device of the present invention to monitor electronically the usage while substantially maintaining a familiar look and feel in a highly miniaturized and portable package. The plastic sanitary cover 220 and end cap 210 are removed from the package 200 as it comes from the manufacturer and discarded. The meter dose dispenser 140 (containing the medicated powder) is placed over tubular boss 111 with key 214 aligned with key slot 112 so as receptive inner surfaces 216 snugly press fit until surface 217 nearly abuts electronic housing 140 at surface 252. The activation sheath 120 is then placed over metered dose dispenser 140 until surface 261 abuts electronic housing 110 at surface 253. The mouthpiece 219 of metered dose dispenser 140 protrudes through opening 264 until surface 262 snugly fits around the tapered body of dispenser 140 housing. At this position, an air tight seal exist between surfaces 263 of the activation sheath 120 and 218 of the metered dose dispenser 140. A detailed operation of these components and how they interact shall be discussed later. The sanitary protective cover 130 of the present invention screws onto electronic housing 110 via receptive threads 271 and 254 respectively, completing the miniaturized portable electronic monitoring apparatus 100.

The components electronic housing 110, activation sheath 120 and sanitary cover 130 of the present invention are plastic elements formed in a conventional manner by those skilled in the art of die and mold making.

It is to be expressly understood that end cap 210 and cover 220 are discarded as the medication dispensing package 200 comes from the manufacturer and replaced with similarly shaped 110 and 130 structures to maintain a streamlined and familiar look and feel. If the streamlined feature were to be forgone, the electronics housing could adjoin conventional dispenser package 200 over end cap 210 with out removing it, or the sanitary cover 220.

In FIG. 3a–3f, the electronic housing end cap 110 of the device 100 is shown in several views, and cross-sectional views, revealing inner chambers and passageways. The electronics access cover 300 mates with electronic housing 110 via receptive threads 301 and 302 providing enclosure of the chamber 320. The cover 300 has hollow inner space 321 to provide maximum chamber 320 size when assembled. Notches 303 allow cover 300 to be tightened fully into housing 110 so as recess 322 accommodates cover wall 304 to be completely flush with housing. A two prong forked tool or conventional needle nosed pliers would access notches 303 and be turned either clockwise or counterclockwise to put on or remove cover respectively to gain access into chamber 320 or to close in, as will be discussed later.

Ambient air inlet 305 allows air to flow into chamber 320 from both sides of the electronic housing 110 and continue up through air passage 310. This function shall be disclosed more fully in FIGS. 4 and 5. The communication connector passage 325 connects chamber 315 and chamber 320. The chamber 320 holds the electronics assembly of FIG. 4 with communication connecter protruding through passage 325 so as to be accessible in chamber 315. There is an electronics assembly key notch 340 which aligns the unit for proper orientation during assembly.

We also see more clearly the key slot 112 in tubular boss 111 and the surfaces 252 and 253 in there relationship to the air passageways 305 and 310. These relationship shall be better understood in FIG. 5. The key slot 1.12 has incorporated into it, a magnet 350 and spring 351. As alignment key 214 of the commercially available medication dispenser 140 engages key slot 112, alignment key 214 pushes (in) against magnet and compresses spring 351. If dispenser 140 is removed from tubular boss 111, the spring would force magnet back out. The purpose of the magnet and spring is to detect when dispenser 140 is in place or removed from system and shall be better discussed in FIG. 7.

In FIG. 4a shows a side view of the electronics assembly 400 comprising; three each multi layer printed circuit boards (PCB) 401 top, 402 middle and 403 bottom, PCB interconnectors 404, electronic circuitry 405, batteries 410, and 411 with battery clips 450 and 451 respectively, communication connector 415, activation sensing elements 435 arid 436. PCB 401, 402 and 403 communicate with one another as may be necessary over the multi-pin interconnectors 404. Assembly and disassembly of the PCB's are accomplished through the mating of these interconnections in a conventional manner as each PCB interconnector has male and female pins and receptive holes as the case may be. In the preferred embodiment, activation sensing elements 435 and 436 are proximity reed switches. These switches responded to mechanically open and close as magnet 122 (embedded in the wall of activation sheath 120 of FIG. 1) comes within the proximity of the magnetic field. Sheath 120 is turned (which also turns dispenser 140 by means of alignment keys 121 and fluted surfaces 141) clockwise and counterclockwise to feature-out a dosage of medication within dispenser 140. As this process is taking place, the reed switches respond to the magnet passing within the proximity. This operation is detailed later. The printed circuit boards, interconnectors, and proximity reed switches and battery clips are all conventional and are manufactured and available by several sources. These components could easily be fabricated by anyone skilled in the art of miniaturized surface mounted technique.

FIG. 4b shows a top view of the assembly 400 indicating the orientation of the major components of circuitry 405 (microprocessor and clock and ram chips are located on the PBC 402). Also are the orientation of interconnectors 404 (which pass through all three PBCs). The external communications connector 415 and activation sensing elements 435, 436 and 437 are on the top surface of PCB 401 as is the main sensing element 425. The PCB assembly alignment key 460 is located on the bottom PCB 403 which aligns assembly 400 to properly fit into chamber 320 of electronics housing 110 as shown in FIG. 3, so as to mate with assembly key notch 340. When properly installed, the communications connector 415 would protrude through connector passage 325 to make connection with external connector cable possible within chamber 315. (Note, dispenser is removed to accomplish external connection to 415, which shall be discussed later). The bottom view of assembly 400 is shown in FIG. 4c with main system batteries 410 being secured to PCB 403 by battery clips 450. Batteries 410 are the main power to the device and are two conventional 3.0 volt lithium cells, model number ECR 2430 as manufactured by Eveready Co. Inc., St. Louis, Mo. Removal of electronic access cover 303, as shown in FIG. 3 would allow replacement of batteries 410 when necessary.

The 3.0 volt battery 411 (shown in FIG. 4a on the top side of PCB 402), is to power the ram memory if main batteries 410 are ever removed or become low in energy. Battery 411 provides non-volatility to date and time clock and ram circuitry. It is manufactured by Renata in Switzerland and available through Renata Batteries U.S., Dallas, Tex. 75207, as part number CR927. This power system assures that all logged records are retained in the ram in the event the main power batteries 410 run down and need to be replaced.

The main sensing element 425 is detailed in partial perspective view of FIG. 4b. The main sensing element 425 is mounted across a hole 426 in the top PCB 401 via wire leads 440 and 441, and soldered electrically to pads 442 and 443 respectively. The main sensing element 425 in the preferred embodiment is a fast response thermistor manufactured by Betatherm Corporation, 910 Turnpike Road, Shrewbury, Mass. 01545, as part No. 100K6MCA24. It is to be expressly understood that any conventional sensing scheme using, for example a pressure device or an audio element device, could be used instead of the thermistor arrangement disclosed above and that the approach shown in FIG. 4d is exemplary of one approach.

Figure 2A:
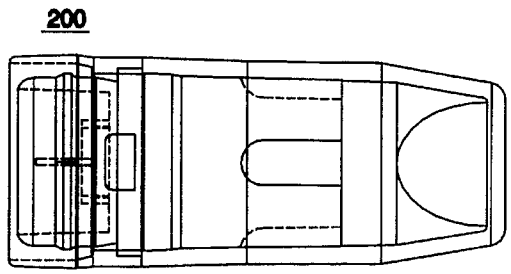
Figure 2B:
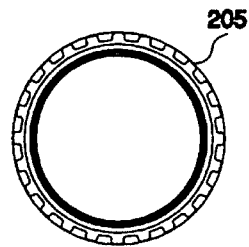
Figure 2C:
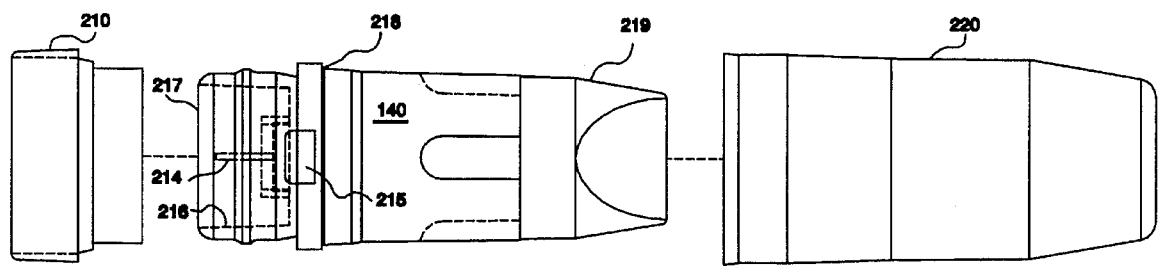
Figure 2D:
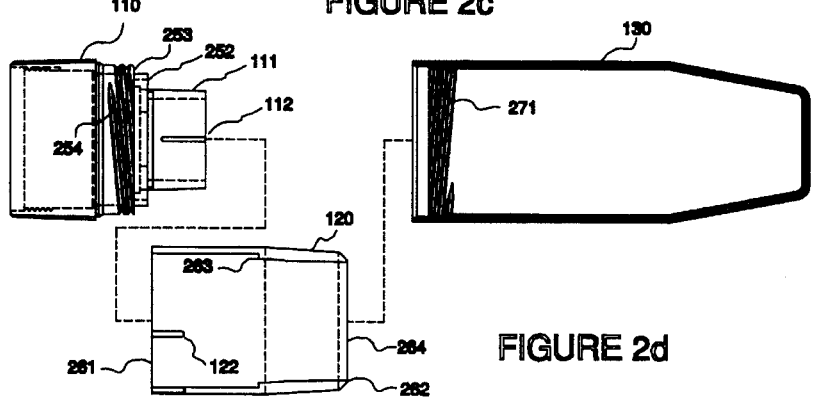
Figure 2E:
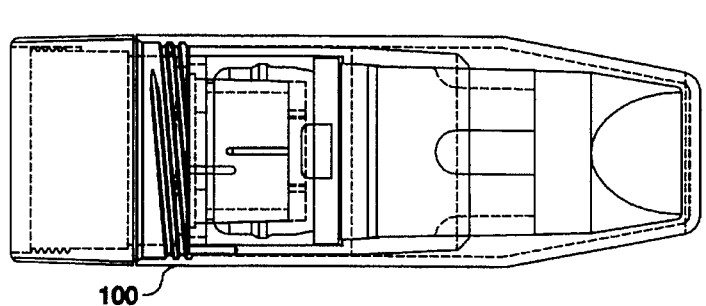
Figure 2F:
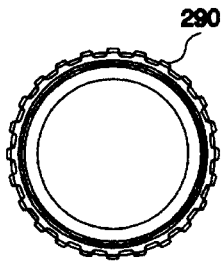
Figure 3A:
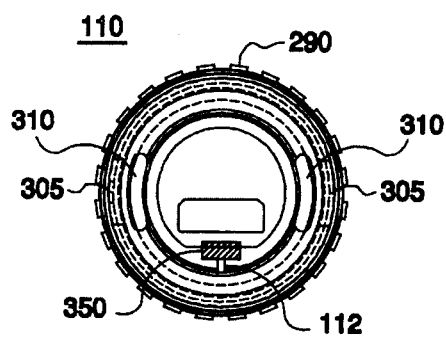
Figure 3B:
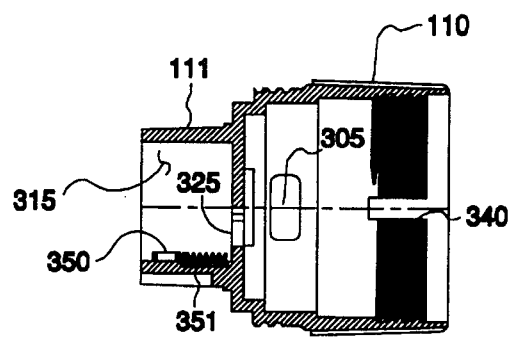
Figure 3C:
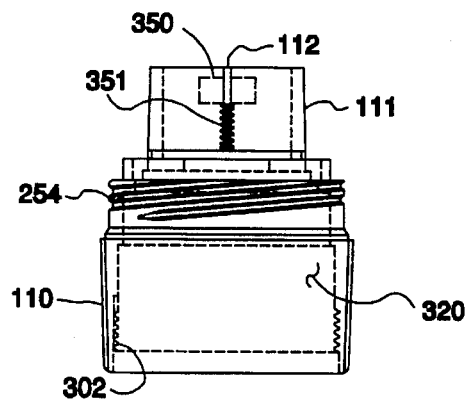
Figure 3D:
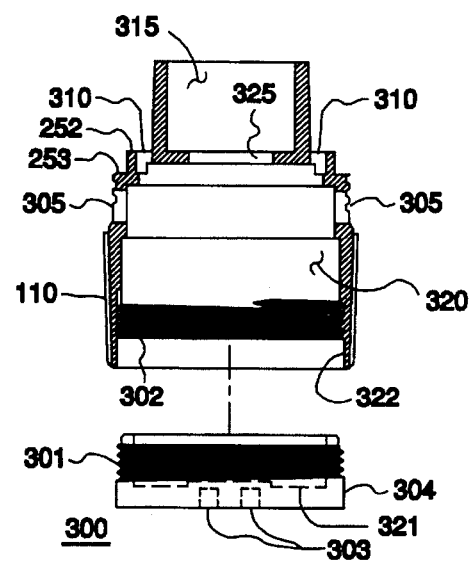
Figure 3E:
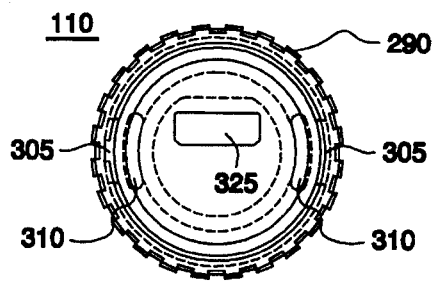
Figure 3F:
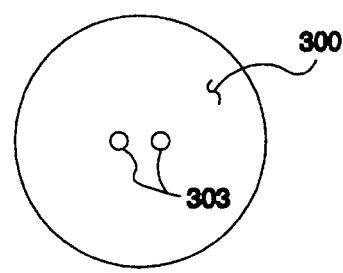

In FIG. 5, is an illustration showing the device 100 of FIG. 2e as it would be used by a patient with sanitation protective cover off, and showing the interrelationships of air passage chambers. Electronics assembly 400 when installed into electronics housing 110 fits tightly in place as PCB 401 abuts housing 110 upper inner surface 505. This tight fit is maintained by access cover 300 pushing against the bottom PCB 403 at cover surface 510. Note also the PBC 402 abuts housing 110 middle inner surface 515 to fully secure the assembly 400 at each of the three PCB's and to provide isolation between the air passageway 305 and 310 via PCB401.

When metered dose inhalant dispenser 140 is installed, as was previously discussed, onto tubular boss 111 and press flitted down so as surface 217 nearly abuts surface 252, and activation sheath properly installed so as bottom surface 261 abuts housing surface 253, an air tight seal is created at sheath inner surface 263 and the body of dispenser 140 at surface 218. When metered dose inhalant dispenser properly installed a substantially air tight cavity 520 (which exist all around the outer bottom position of dispenser 140 within the inner bottom portion of sheath) is created.

In operation, the apparatus 100 with conventional medication metered dose dispenser installed is placed in between the lips of a user at mouthpiece surfaces 219. The user would inhale and in doing so, draw ambient air through the system beginning at inlets 305. The air must pass through PCB 401 at the hole 426 as shown in FIG. 4b and 4d (which is oriented 90 degrees from the two inlet 305) within chamber 320 before exiting through air passageways 310 into cavity 520 because of the tight fit of the PCB circumference against housing inner surface 505. The air low continues up through the inlets 215 (which is again oriented 90 degrees from the two inlet 310) of the dispenser 140. Ambient air, once inside the metered dose dispenser 140 passes through inner chamber to "pick-up" a metered dose of dry powder medication before exiting through mouthpiece 219 orifice 145 to be inhaled into the user's mouth. A further discussion of this operation shall be detailed later after disclosure of the electronic function.

Figure 6:
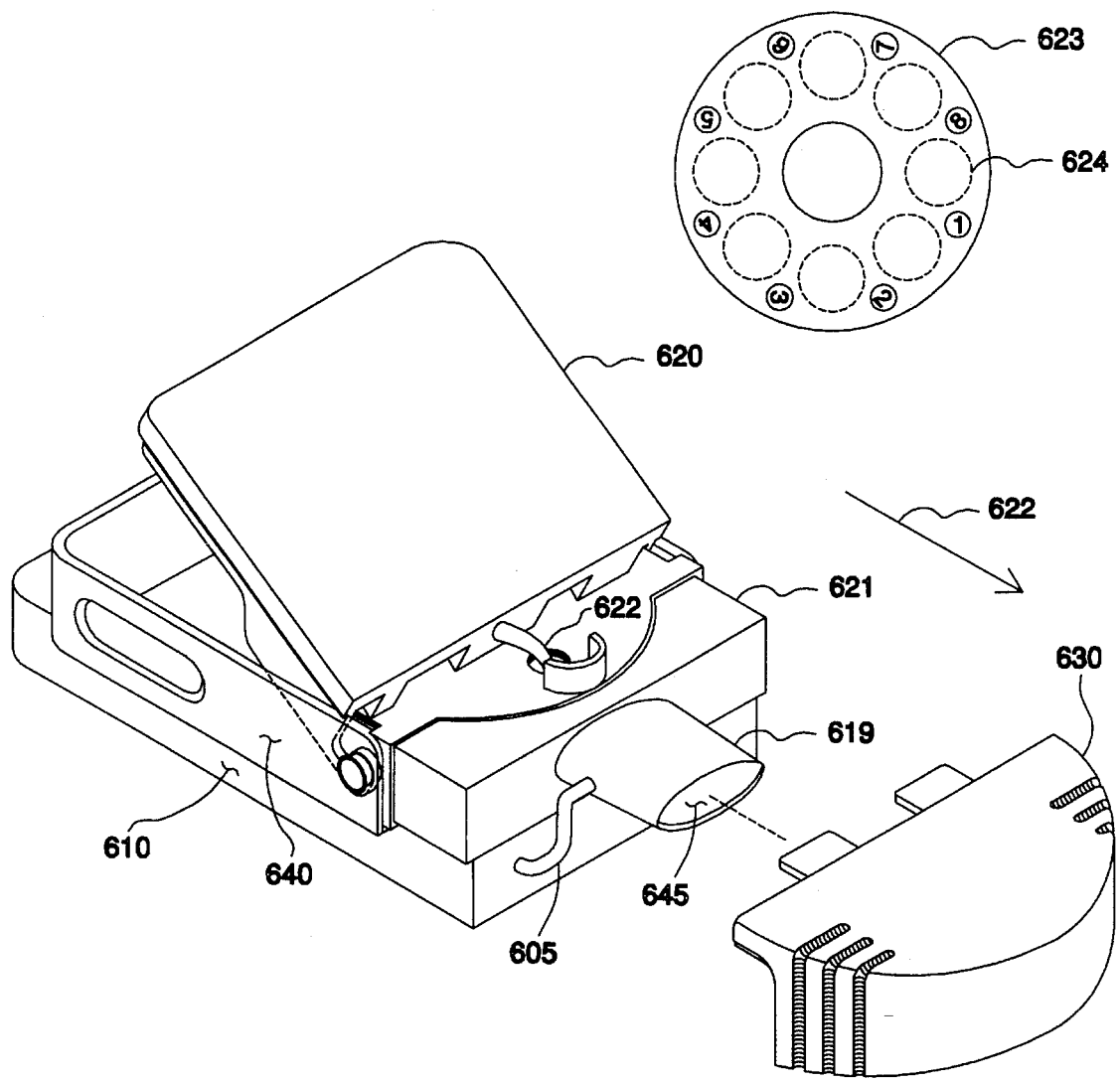

In FIG. 6, sets forth a perspective illustration of an alternate embodiment showing a different manufacturer of conventional dry powder medication inhalant package 640, that s manufactured by Glaxo B.V., Wattbaan 51, 3439 ML Nieuwegein. This configuration dispenser 640 is known as the Diskaler®. The replaceable, eight dosage disk 623 would be inserted into dispenser 640 each time the medication within the eight blister positions where depleted. Electronic housing 610 is affixed to dispenser 640 and with air passageway 605 to mouthpiece 619. The activation cover 620 shown in the up, activate position) has a puncher pointer 122 which pierces the thin film on blister disk 623 at one position 624 for each time medication is desired. The medication blister disk 623, has eight positions 624 and is installed in dispenser 640 with its activation cover closed (down), and slide draw 621 pulled out in the direction of arrow 622. To advance the disk 623 to each of the eight positions, the slide draw 621 is likewise pulled out and then back in to position an unused blister containing medication dry powder in front of the puncher pointer 622.

In operation, the user would remover sanitation cover 630, position unused blister position 624 by sliding draw 621 out until it abuts a mechanical stop and then back in, then left activation cover 620 with puncher pointer 622 thereon, to pierce the thin film exposing the medication at one of the eight positions 624. Mouthpiece 619 would be placed between user's lips and upon inhaling, would draw the medication dry powder through passageways in dispenser not shown and out orifice 645. Air passageway 605, activation cover 620 and slide draw 621 with disk 623 present are monitored similar in principle by electronics within housing 610 as air passageways 305, activation sheath 120 with dispenser 140 present are monitored by electronics within housing 110.

It is expressly understood that the electronic dry powder medication dispensing monitor and chronolog apparatus 100, although shown here in detail in the preferred embodiment and an alternate embodiment, and may be configured to electronically monitor and chronolog other conventionally manufactured dry powder dispensers as they may become available, and that the present invention is not limited to the configuration of any particular manufacturer of dispenser of dry powder medication.

Figure 7:
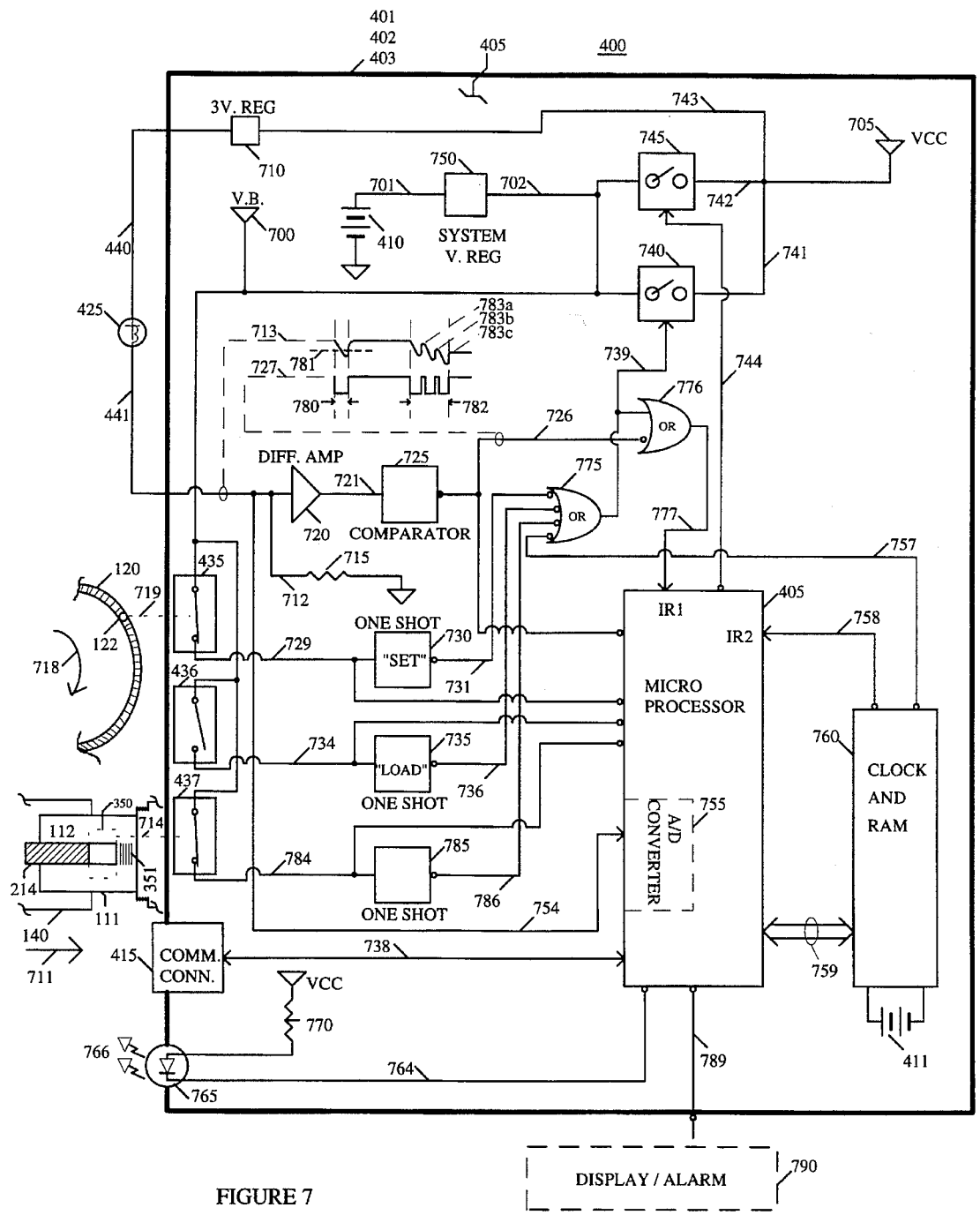

In FIG. 7 is disclosed a schematic block diagram of the electronic circuitry 405 on printed circuit top 401, middle 402 and bottom 403 boards of the electronic assembly 400. Main system battery 410 supplies a constant source of power to the input of system voltage regulator 750 over regular source line 701. The regulated output of 750 supplies system battery power over common line 702 to proximity reed swatches 435, 436 and 437, and is voltage V.B. source 700. Common line 702 is also available to the inputs of electronic switches 740 and 745. The V.B. 700 source is a constant supply of standby power to all essential circuitry (connections not shown) in addition to what is shown, The essential circuitry are components which initialize the process of detecting events and shall be discussed in detail later in this section.

The output of proximity reed switch sensor 435 is connected to condition "set" one-shot 730 over line 729 and further connected to microprocessor 405 I/O port. The output of reed switch sensor 436 is connected to condition "load" one shot 735 over line 734 and further connected to microprocessor 405 I/O port. Likewise, the reed switch sensor 437 output is connected to condition "dispenser present" one-shot 785 over line 784 and further connected to microprocessor 405 I/O port. The output of the "set" one shot 730 is connected to OR circuitry 775 input over line 731. Likewise, the output of the "load" one-shot 735 is connected to the OR circuitry 775 input over line 736. And further the output of the "dispenser present" one-shot 785 in connected to the OR circuitry 775 input over line 786. The output of OR circuitry 775, over common line 739, is connected to control gate of electronic switch 740 and OR circuitry 776 input. The output of 776 is connected to microprocessor 405 interrupt No. 1 (IR1) input 777. The output of electronic switch 740 provides operation power to the system voltage Vcc 705 supply over line 741. The Vcc 705 source provides power to all circuitry (non standby) which has been shut off to conserve energy. Vcc 705 connection lines are not shown on the schematic block diagram. Once Vcc 705 has been brought up to power as the proceeding paragraphs shall detail, it is latched-on by instruction of the microprocessor as shall be discussed later in this section. To illustrate the function of the circuitry thus far, when a commercially available medicated dry powder dispenser 140 has been affixed to tubular boss 111 so as to properly engage alignment key 214 into key slot 112, magnet 350 is pushed inwardly compressing spring 351 in the direction of arrow 711. The magnetic field 714 of magnet 350 causes proximity reed switch sensor element 437 to close and standby power V.B. 700 activates condition "dispenser present" one-shot to generate a momentary pulse to OR-ing circuitry 775. This in turn activates electronic switch 740 to provide Vcc power 705 to the system for as long as the duration of the momentary pulse generated by one shot 785 (for example 100 milliseconds). The sheath 120 of the electronic medicated dry powder inhalant chronolog apparatus 100 is rotated with respect to electronics housing 110, either clockwise or counterclockwise, the magnetic field 719 of magnet 122 (which is embedded in the wall of sheath), moves within the proximity of reed switch sensing elements 435 and 336 to cause activation of one or the other. When in the "set" position, V.B. 700 standby voltage is first available on line 729, functions "set" one-shot 730 so as to provide a momentary pulse to the OR-ing circuitry 775, Likewise, if the sheath 120 is rotated with respect to housing 110 in the direction of arrow 718, so as the embedded magnet 122 to be in the proximity of reed switch sensing element 436, magnetic field 719 causes activation of 436 to occur. The standby power V.B. 700 becomes available over line 734 to function the "load" one-shot 735. A momentary pulse output is over line 736 effecting OR circuitry 775 and electronic switch 740 similarly to one-shot 785 as described earlier to provide system power Vcc 705. The positions "set" and "load", as is determined by sensors 435 and 436 respectively, are indicative of a metered dosage of medication being available to inhale. Further description of these functions shall be described later in the section.

The clock and ram circuit 760 further functions to activate the OR circuitry 775 over line 757. Clock and ram circuitry 760 has its own independent standby power source battery 411. Battery 411 functions to operate the time and date clock at very low levels of energy in addition to maintaining stored data in the ram (random access memory) section of circuitry 760 during periods of main system power Vcc 705 shutdown, as will be fully discussed later. The clock and cram circuit 760 can be pre-programed to cause a pulse on line 757. This pulse presented to the input of OR circuitry 775 functions to activate electronic switch 740 providing regulated power to Vcc 705 similarly to functions previously described with one-shots 785, 730 and 735. All four of these circuits; 785, 730, 735, and 760 serve in part to activate electronic switch 740 momentarily making system battery voltage available from regulator 750 to energize main system power Vcc 705.

Any time main system power Vcc 705 is activated all associated circuitry which was shut-down to conserve battery energy, comes alive and functions according the rom (read only memory) program stored within microprocessor 405. Upon initialization of microprocessor 405, program instructions command electronic switch 745 to activate over line 744. System regulated voltage is now also provided to Vcc 705 over line 742. The purpose of electronic switch 745, as previously discussed, is to "latch ON" main system power Vcc 705 to all appropriate circuitry to function programed instructions beyond the momentary pulsing activation interval generated at the output of OR circuitry 775 as was earlier described.

The 3 volt regulator 710 becomes active (over line 743 when system Vcc 705 is powered supplying current over lead 440 of fast response thermistor 425. Thermistor 425 is further connected to input of differentiating amplifier 720 on lead 441 and to microprocessor 405 analog to digital (A/D) converter 755 input by line 754 The input of differentiating amplifier 720 is also connected to "ground" potential through current limiting resister 715 over line 712. Differentiating amplifier 720 output is connected to comparator 725 over line 721. The function of amplifier 720 in part, is to "track" the slope of wave form 713. Comparator 725 outputs square waive signal 727 at threshold 781. The threshold 781 shall be discussed in detail later. Signal 727 is presented to the OR circuitry 776 and the microprocessor 405 I/O over common line 726 similarly as OR circuitry 775 inputs as was described earlier.

Microprocessor 405 once initialized, responds to signals presented at its interrupt inputs IR1 and IR2. IR1 signal over line 777 is indicative of activity generated by proximity reed switch sensing elements 435, 436 and 487, and by the main sensing element 425. The microprocessor 405 will scan I/O ports to see which one of lines 729, 734, 784 or 726 has toggled and shall proceed to predetermined programed instructions based on which line is active. Additionally, when signal is present on common line 726, microprocessor 405 activates function of its internal A/D converter 755 to be responsive to any analog signal present over line 754. The result of signals, present on 754, 721, and 726, and their characteristics 780, 781, and 782 are due to the activation and dispensing medicated dry powder inhalant, and shall be more detailed later under the operations section of the present invention. The IR2 interrupt input of microprocessor 405 responds to activation generated from the clock function of clock and ram circuit 760 over line 758. This interrupt is indicative of some predetermined programed instruction, for example, "alarm" to take medication. Line 789 delivers informational data, instructions and alarm signals from microprocessor 405 to device 790 (which shall be further discussed in FIG. 10 herein. Data and address lines 759 are conventionally connected between microprocessor 405 and clock and ram circuit 760, and functions as necessary according to conventional programming technique. Valid event LED (light emitting diode) indicator 765 illuminates when microprocessor 405 toggles output line 764. Current limiting resistor 770 functions to complete LED indicator 765 circuit. Illumination 766 serves as feedback to the user of the electronic inhalant apparatus 100 when optional display/alarm device 790 is not present. It is understood that a tone generator could be substituted for an audible effect instead of the visual effect of the LED 765 circuit or both Finally communications connector 415 is connected to the microprocessor 405 over by-directional transmit/receive line 738. Connecter 415 also provides external system power directly to Vcc 705 (not shown) when an external communications cable is connected to the electronic inhalant apparatus 100 conserving battery life. This feature shall be further discussed in FIG. 9.

All components illustrated in schematical block diagram in FIG. 7 are representative of functional components and are commonly available in a diversity of configurations by many manufacturers. Such components are easily connected to one another by anyone skilled in the art as set forth in the diagram of FIG. 7. It is to be expressly noted that while individual sensor elements have been set forth and discussed for electronics shown in FIG. 7, in the preferred embodiment, other sensor elements may be substituted to result in the same function. For example, thermistor sensors 425 which detects change in temperature as ambient air flows through air passages created by the user inhaling and producing wave form 713, could be produced by an audio element (and appropriate associated circuitry) detecting change of sound as air flows in passages in the approximate path of sensing element 425. The signature of the sound, both sonic and ultrasonic created by first, as the air is drawn into and through the inlets, holes and passages 305, 426, 310, 520 and into 215, second out of mouthpiece 219 and dispensing outlet 145 would have exact and repeatable signature characteristics. Or one further example, pressure or peizo sensors detecting changes in pressure as air flows through said passages in the path of sensor elements 425. These and other sensor element schemes all could be made to produce similar wave forms 713 and 727 and A/D signals present on lines 754, to provide input signals of the present invention. Also, the reed switches 435, 436 or 437 of the preferred embodiment could be hall effect switches or micro switches, for example, producing similar functionality.

Figure 8:
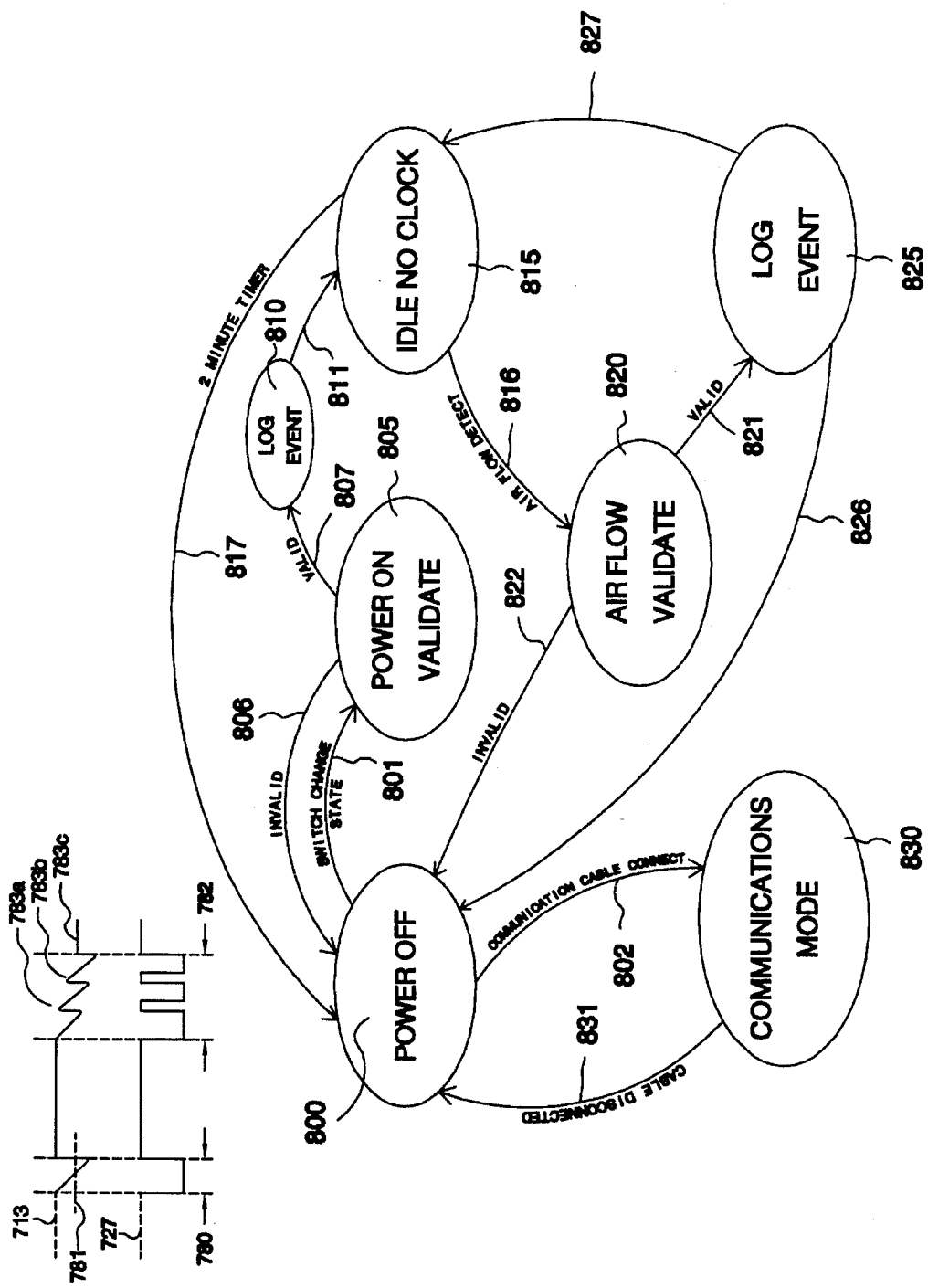

In FIG. 8, is set forth the flow of logic in the form of a state table concerning the sensing elements for the operation of the electronic circuitry 405. This process is driven according to instruction program code conventionally written as executions recommended by components manufacturer's data sheet recommendations for any desired result as may be capable of the components, and anyone skilled in the art could write such code. In FIG. 8, the following occurs. Power off state 800 normally exists in a standby mode. In the event an activity is sensed, such as a detected reed switch 435, 436, or 437 activation, the power off state 800 enters the power on validate state 805 over path 801. It is in this state, that the electronic switch 740 activates system power Vcc 705 to provide momentary power to system to determine the validity of the activation. If proper activation is detected the system would latch electronic switch 745 and enter log event state 810 valid over path 807. If improper activation occurs, the system would shut-down to standby mode power off 800 over path 806. Once event has been logged in state 810, the system would enter idle state 815 and begin a "wait" routine lasting, for example 2 minutes. Here is where the thermistor element 425 is expected to be sensing the function of the user inhaling. If no activity is sensed, and after the expiration of the wait period, the system would shut-down from the idle state 815 to standby mode power off state 800 over path 817.

If the result of signals on lines 726, 721, 754, and their characteristics 780, and 781 meet the criteria wave forms 713 and 727 of FIG. 7, indicating an air flow inhalation, the air flow validate state 820 is entered. This sensed activity must be in synchronization with the proper sequencing of reed switch 435 and 436 to enter the log event state 825 as valid over path 821. Else, the system goes back to standby mode power off 800 over path 822. From log event state the system would shut-down to standby mode power off 800 over path 826 if all proper criteria is met. Else, system would enter back to idle state 815 over path 827 to await further activity. All events would be logged in memory complete with date and time, and magnitude of signal present on line 754 indicating the strength of inhalation. If criteria wave form 713 and 727 are not the expectant shape, slope, magnitude and minimum threshold level 781, the system would flash LED/display/alarm as necessary according to system configuration via 765 and/or 790.

It is important to understand that the "validate signals" are part of the management of state 805 and 820, and as such determines if the activation of the apparatus 100 is indicative of medicated inhalant being properly dispensed in user's mouth or otherwise not properly sequenced indicating no medication has been dispensed.

From each of the validate state 805 and 820 or, log event states 810 and 825 the system enters into the flash LED/display/alarm state (not shown) to provide feedback of the event to the user before entering back to the power off state 800 for standby shut-down. The flash LED/display/alarm state may be entered directly from the standby 800 mode, as is in the case of clock and ram circuit 760 of FIG. 7, would initialize upon a predetermined programed schedule to remind user to take medication.

It should be explicitly understood, that flash LED/display/alarm state is symbolized as a general system configuration. It may be as simple as the LED indicator 765 or more complex as display 790 (which shall be elaborated in second embodiment of FIG. 10 in detail), or may not exist at all. In the later case, upon completion of logging event, system would return to standby power off 800. This later case is a zero feedback configuration which is desirable in "blind testing" patients to serve as medication dispensing behavior analysis.

Importantly, the teachings of the present invention provides feedback to the user as may be necessary. For example, apparatus 100 having installed a placebo dry power dispenser 140, is useful for helping new patients to get use to the timing in activation of the device and inhaling. The flash LED/display/alarm and sensor capability would indicate such feedback as; improper synchronization of inhaling and magnitude, inhaling too slow or too fast, and inhaling too hard or too soft for example. All events are monitored and logged. Once the new patient was comfortable with proper operations of self administering the inhalant, they could use a less complex display 765 instead of 790 configuration of the apparatus 100.

To illustrate further the sensing elements and associated circuitry, the power on state 805 would be entered from standby power 800 over path 801 for each of the events indicated in time reference 782. Time 782 is a possible wave form indicating 3 valid recursive actuations of the electronic inhalant apparatus 100. Note that each recovery peak 783a, 783b and 783c becomes less and less from the original starting temperature as is indicated at the start of time at wave form 782 of signal 713. By means of differentiating amplifier 720 in FIG. 7, the threshold 781 is proportionally to each descending starting point of recursive activations 783b and 783c respectively. Wave form 727 of time 782 indicates that proper threshold criteria has been meet for each activation and would have entered air flow validate state 820. This together with signal present on line 754 as interpreted by A/D converter 755 would constitute a valid magnitude of signal indicating a proper inhalation (or less than proper inhalation as the case may be), and log event in state 825. If less then full proper inhalation is discerned, which would be indicated in the feedback LED/display/alarm (as may be possible when user does not breath-in fully, or near fully), would prompt user to inhale through apparatus 100 a second, or in the case of the above illustration a third time. For each of the three activations in the above illustrated example, the full cycle from powering up, validating signals, logging events, and as may be appropriate flashing LED or displaying or alarming, to power shut-down or to wait in idle state 815 would occur between each recursive activation because of the speed and efficiency of electronics assembly 400.

Similarly, when system activation is due to activity responsive to proximity reed switch sensor 437, the power on validate state 805 would be entered and further enter state 810 to log event and give any feedback of event via 765 or 790 as may be appropriate, for example, date and time new dispenser 140 is installed.

When communications connector 415 has been connected to external data retrieval device (disclosed in FIG. 9), system enters into communication mode state 830 over path 802 and system becomes responsive to the external commands. The down loading of possible entries would be; interval schedule of medication for auto alarm indication, quantity of dosage, type of medication, and patient's name. The up-loading function would extract all chronologically stored data including an instrument diagnostic report listing sensor behavior and battery supply voltage levels. These features shall be discussed further in the disclosure of the present invention in FIG. 9, 10 and in operations. The powering of system Vcc 705 of FIG. 7 is supplied directly from external source via connection to communication connector 415. Once disconnection from communication connector 415 happens, the communications mode state 830 returns back to the power off state 800 and shuts-down to standby mode over path 831.

Figure 9:
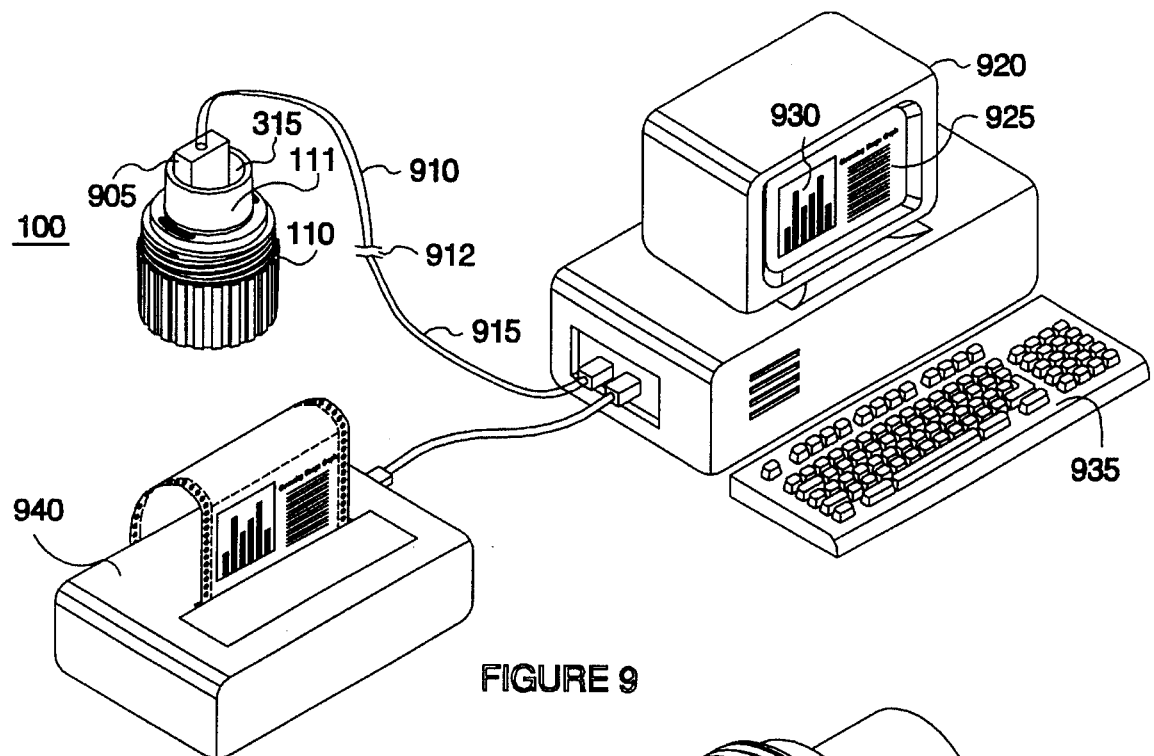

In FIG. 9 the electronic dry powder inhalant chronolog apparatus 100 is shown with the dispenser 140 removed and revealing tubular boss 111. Within tubular boss 111 in chamber 315 is access to the communications connector 415, as identified in FIG. 4a and 4b, shown here with external cable 910 and cable connector 905 properly attached to the apparatus. Communications cable 910 and 915 attach to computer 920. The junction 912 illustrates that communication modems may be in the data path transmission over cables 910 and 915 for remote retrieval of chronolog stored records. Computer 920 accesses the data base in the chronolog apparatus 100 for retrieval and analysis of the medication administered and is displayed in tabulated statistical form 925 and graphically as in 930. Such information may be stored in computer memory for combining with other similar chronolog users data and further printed to hard copy utilizing printer 940. Keyboard 935 is manipulated in conventional manner to program apparatus 100 for scheduling if required by doctor. Retrieved information 925 and 930 also could represent a diagnostic report of the apparatus 100 over the full recorded period of time which includes battery and sensor response. This information, under analysis, indicates if the instrument was functioning properly. The computer, printer, cabling and connectors are all conventional and well known and are easily operable by anyone skilled in data handling.

The emphasis here is that positive reporting of prescribed medication is diligently recorded and analyzed to assure the benefits of the medicine doing what the doctor prescribes based on reliable feedback information.

Figure 10:
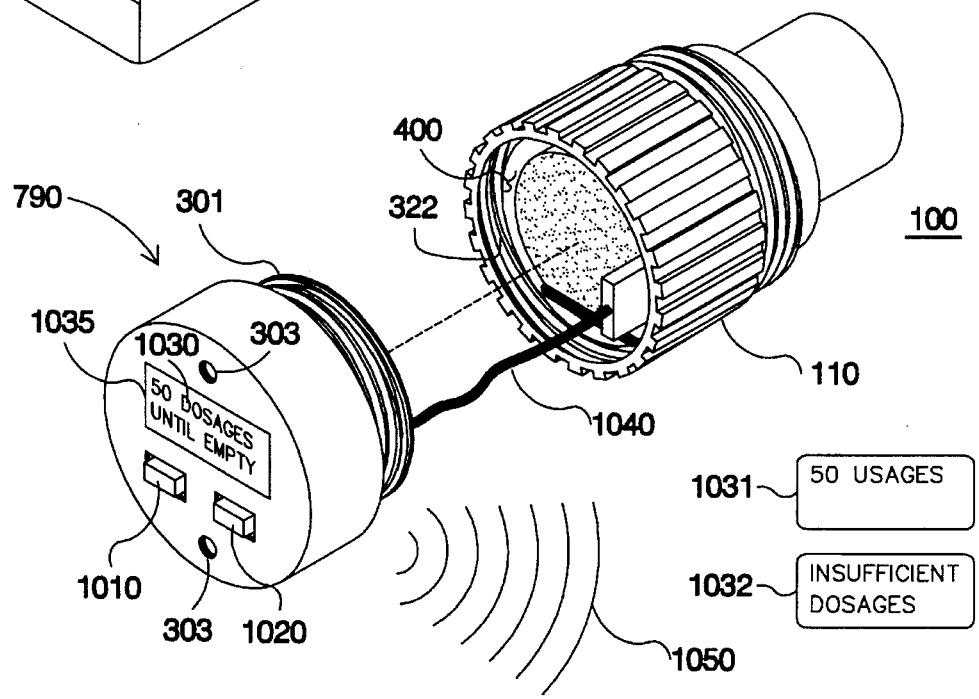

In FIG. 10 is shown a second embodiment of the present invention where display/alarm module 790 replaces the electronic access cover 300. This miniaturized module 790 attached to the electronics housing 110 as was similarly disclosed in FIG. 3 utilizing threaded surfaces 301 and 322.

The LCD (liquid crystal display) 1035 and push-bottoms 1010 and 1020 are interconnected to microprocessor 405 over wire and connections 1040 conventionally and respond to diverse program routines. One example of such routine is when the user would depress menu selection push-button 1010 until desired option appears in the display 1035, for example (NUMBER OF DOSAGES REMAINING). The user would then depress activate request push button 1020 for the response to the request, for example (50 DOSAGES UNTIL EMPTY) message 1030. The apparatus could know this information if it were programed with the typical number of metered dosages as is purported by the medication manufacturer. Else the display would simply indicate, for example, (10 DOSAGES USED THIS CONTAINER) as a message 1030. Other example messages are indicated as 1031 and 1032.

It is expressly understood that the type and meaning of messages 1030 and audible alarms 1050 indicated and displayed by module 790 is as varied as medications and concerns that doctors may have, and that the present invention contemplates, and is suited to deliver fully, utilization to satisfy the need.

In operation, the present invention apparatus 100, being miniaturized, portable and having a familiar shape as is in FIG. 2e, to users as a non electronic medication inhaler dispensers (FIG. 2a), the user would install a conventional medication dry powder dispenser 140 onto electronics housing 110 with sheath 120, all in proper alignment for the dispensing of medication. Proximity reed switch 437 senses the dispenser being present in system and event is logged in non-volatile memory 760.

As user desires a dose of medication, apparatus 100 (which fits easily in palm of hand) oriented up-right as in FIG. 5, would rotate electronic housing 110 holding on to groved hand grips 290, first clockwise with respect to sheath 120, then back counterclockwise to full mechanical stops for each rotation. Then place mouthpiece 219 positioned such within that user's lips around surface of mouthpiece so as to have dispenser outlet 145 directly accessible to user's inner mouth and throat. The user would inhale one metered dose of medication from dispenser 140.

The rotation as indicated above "loads" the metered dose dry powder as a function of dispenser package 140 and in doing so, makes available the medication for inhalation. Sensors 435 and 436 detects this exact procedure. For example, if clockwise rotation to load medication is not fully rotated to engage mechanical stop, reed switch 437 would not activate and no medicated dry powder is available for inhalation. Apparatus 100 would log such "missed" event and if so configured, alert user of improper usage and instruct to repeat procedure.

During powering up, caused by the rotation discussed above, the fast response thermistor element 425 self heats and when the ambient air, caused by inhalation through the apparatus into inlet 305, air passes through air hole 426 of PCB 401, would experience a drop in temperature of the fast response temperature thermistor 425 which would respond to the slightest deviation from its self heating condition. If no air is being drawn through ambient air inlet 305, the rate of temperature would continue to rise, or be steady. The A/D converter 755 monitors these fluctuations and characteristics which determine proper inhalation. A further example, is of a user with little lung capacity, a very low magnitude of inhalation would be sensed, and would prompt the user to inhale a second or third time (as was described in a previous example), to fully "pick-up" all of the medication available in the prescribed dispensed dosage.

The physical time of actuation rotation and inhalation is monitored and system would power down if activity is not fully executed. At the leading edge of the any detected activity, the microprocessor 405 has been initialized and latched operation power via electronic switch 745. Validation of signals generated by the positive rotation to mechanical limits and differentiating amplifier 720 and comparator 725 is processed together with A/D converter 755 signals to determine that positive medication dry powder has been "loaded", and the strength with respect to magnitude of inhalation has occurred.

An important feature of the present invention is expressly understood that the user is identified as positively inhaling the medication by the apparatus as prescribed. This is defined as the medication being administered into the user's mouth as intended in full dosage. For example, the only way to cause a rapid drop of temperature experienced by sensor 425 is to inhale through the apparatus, and the only way to make available a metered dose of dry powder medication is to execute proper rotation of dispenser with respect to electronics housing, thus exact positive monitoring the administration of drugs into the user is achieved and chronologically recorded. The fast response sensor 425 would produce different wave form characteristics then those disclosed in referenced time 780 and on A/D signals of line 754 of FIG. 7 if procedure is not exactly adhered to. This is possible by the distinct signature developed by the user drawing ambient air through inlet 305, hole 426, passage 310, cavity 520 and into dispenser inlets 215 before being exited out mouthpiece 219 outlet 145. Thus, if accidental actuation, or misuse of apparatus occur's, appropriate event recording is chronologged and further, complete positive analysis is possible by the prescribing doctor.

While the preferred embodiments of the present invention have been disclosed and shown, it is to be understood expressly that modifications and changes may be made thereto and that the present invention is set forth in the flowing claims.

The embodiments of the invention for which an exclusive privilege and property right is claimed are defined as follows:

1. A dry powder inhalant device adapted for mounting on a conventional medication dry powder dispenser having a mouthpiece incorporated in one end of the dispenser, the device designed for monitoring prescribed dosages of dry powder received through a mouthpiece of a dispenser, through the lips and into the mouth, throat, and respiratory system of a user of the device, the device comprising:

dry powder sensing means mounted inside an electronic housing, said electronic housing adapted for attachment to a dispenser, said dry powder sensing means for sensing the release of dry powder in a dispenser;

dry powder signal generating means connected to said dry powder sensing means, said dry powder signal generating means for electrically signaling when dry powder is released in a dispenser;

air flow sensing means mounted inside said electronic housing and disposed adjacent an air inlet in said electronic housing, said air flow sensing means for determining the flow rate of air through the air inlet, said air flow sensing means also for determining the air flow rate through a mouthpiece of a dispenser and sensing the duration of the air flow therethrough;

air flow signal generating means connected to said air flow sensing means, said air flow signal generating means for electrically signaling the rate and duration of the air flow; and display means connected to said dry powder signal generating means, said display means for displaying each occurrence of the release of dry powder in a dispenser, further said display means connected to said air flow signal generating means, said display means for displaying each occurrence of air flow from said air inlet in said electronic housing, an air flow rate through a mouthpiece of a dispenser and the duration of an air flow through a mouthpiece in a dispenser;

computing and recording means mounted in said electronic housing for logging positively when dry powder is released, when the air flow is received in said electronic housing and through a mouthpiece and the rate of airflow; and a dry powder dispenser sensing means for sensing when a dry powder dispenser is received and removed from said electronic housing, said dry powder dispenser sensing means connected to said computing and recording means for logging when a dry powder dispenser is received and removed.

2. The device as described in claim 1 further including a remote retrieval and data processing means electrically connected to said computing and recording means for retrieval of chronology stored data such as determination of and duration of the dry powder dosages of medication positively dispensed over a period of time and patient related data for analysis by a doctor.

3. A dry powder inhalant device adapted for mounting on a conventional medication dry powder dispenser having a first end and a second end with a mouthpiece incorporated in the first end of the dispenser, the dispenser having an activation sheath received around and secured to a portion of the dispenser, the device designed for monitoring prescribed dosage of dry powder received through a mouthpiece of a dispenser, through the lips and into the mouth, throat, and respiratory system of a user of the device, the device comprising:

an electronic housing adapted for releasable attachment to a second end of a dispenser;

a first and second proximity reed switch disposed inside said electronic housing and responsive to rotation of a sheath and dispenser a fixed distance in one direction on said electronic housing, and rotation of a sheath and dispenser a fixed distance in an opposite direction, said first and second proximity switches sensing the release of dry powder in a dispenser;

dry powder signal generating means connected to said first and second proximity reed switches, said dry powder signal generating means for electrically signaling when dry powder is released in a dispenser;

a fast response temperature thermistor mounted inside said electronic housing and in an air flow path from an air inlet in said electronic housing to a mouthpiece of a dispenser, said fast response temperature thermistor for sensing the rate and duration of air flow introduced and mixed with released dry powder;

an air flow signal generating means connected to said fast response temperature thermistor, said air flow signal generating means for electrically signaling the rate and duration of the air flow through a mouthpiece of a dispenser; and computing and recording means mounted in said electronic housing for logging positively when dry powder is released, when an air flow is received in said electronic housing and through a mouthpiece, and the airflow rate.

4. The device as described in claim 3 further including an electronically operated proximity reed switch disposed in said electronic housing for sensing when a dispenser is received on and removed from said electronic housing.

5. The device as described in claim 3 further including programmable display means for displaying the number of dry powder dosages taken, the number of dry powder dosages remaining in a dispenser, the determination of each dry powder dosage received from a dispenser, the air flow rate received through said housing and a mouthpiece of a dispenser and mixed with the dry powder dosage, said programmable display means connected to said computing and recording means.

6. A dry powder inhalant device adapted for mounting on a conventional medication dry powder dispenser having a mouthpiece incorporated in one end of the dispenser, the device designed for monitoring prescribed dosages of dry powder received through a mouthpiece of a dispenser, through the lips and into the mouth, throat, and respiratory system of a user of the device, the device comprising:

dry powder sensing means mounted inside an electronic housing, said electronic housing adapted for attachment to the dispenser, said dry powder sensing means for sensing the release of dry powder in a dispenser;

dry powder signal generating means connected to said dry powder sensing means, said dry powder signal generating means for electrically signaling when dry powder is released in a dispenser;

a fast response temperature thermistor mounted inside said electronic housing and in an air flow path from an air inlet in said electronic housing to a mouthpiece of a dispenser, said fast response temperature thermistor for sensing the rate and duration of air flow introduced and mixed with released dry powder;

an air flow signal generating means connected to said fast response temperature thermistor, said air flow signal generating means for electrically signaling the rate and duration of air flow through a mouthpiece of a dispenser; and computing and recording means mounted in said electronic housing for logging positively when dry powder is released, when an air flow is received in said electronic housing and through a mouthpiece of a dispenser and the airflow rate.

7. The device as described in claim 6 further including a remote retrieval and data processing means electrically connected to said computing and recording means for retrieval of chronology stored data such as determination of and duration of the dry powder dosages of medication positively dispensed over a period of time and patient related data for analysis by a doctor.

8. The device as described in claim 6 further including display means connected to said dry powder signal generating means, said display means for displaying each occurrence of the release of dry powder in a dispenser, further said display means connected to said air flow signal generating means, said display means for displaying each occurrence of air flow from said air inlet in said electronic housing, an air flow rate through a mouthpiece in a dispenser and the duration of the air flow through a mouthpiece in a dispenser.

* * * * *